United States Patent [19]

Ireland

[11] Patent Number: 5,048,044
[45] Date of Patent: Sep. 10, 1991

[54] OPTICALLY PUMPED LASERS

[75] Inventor: Clive L. M. Ireland, Warwickshire, United Kingdom

[73] Assignee: Lumonics, Ltd., Rugby, United Kingdom

[21] Appl. No.: 448,123

[22] Filed: Dec. 11, 1989

[30] Foreign Application Priority Data

Dec. 22, 1988 [GB] United Kingdom ................. 8829875

[51] Int. Cl.$^5$ ............................................. H01S 3/06
[52] U.S. Cl. ...................................... 372/66; 372/70; 372/75
[58] Field of Search ....................... 372/70, 72, 75, 98, 372/99, 102, 6, 66

[56] References Cited

U.S. PATENT DOCUMENTS

| 3,196,366 | 7/1966 | Simpson | 372/71 |
| 3,222,615 | 12/1965 | Holly | 372/66 |
| 3,297,957 | 1/1967 | Merkl | 372/66 |
| 3,308,395 | 3/1967 | Sorokin | 372/66 |
| 3,538,453 | 11/1970 | Miller | 372/70 |
| 4,710,940 | 12/1987 | Sipes, Jr. | 372/75 |
| 4,756,002 | 7/1988 | Ruggieri et al. | 372/70 |
| 4,757,513 | 7/1988 | Fukae | 372/99 |
| 4,785,459 | 11/1988 | Baer | 372/70 |
| 4,799,748 | 1/1989 | Brown | 350/96.1 |
| 4,829,529 | 5/1989 | Kafka | 372/6 |

FOREIGN PATENT DOCUMENTS 0138411 4/1985 European Pat. Off. ................. 372/6

OTHER PUBLICATIONS

Diode Laser-Pumped Solid-State Lasers, Fan, T. Y., and Byer, R. T., IEEE J of Quant Elect, vol. 24, No. 6, p. 895, 6/88.
Advances in Diode Laser Pumps, Streifer, W. et al., IEEE J of Quant Elect., vol. 24, No. 6, p. 883, 6/88.
100 mW Laser Diode Pumped Nd:YAG Laser, Smith, R. J. et al., SPIE, vol. 247, p. 144, Advances in Laser Engineering & Applications.
Laser Diode Side Pumping of Neodymium Laser Rods, Hanson et al., App Opt., vol. 27, No. 1, p. 80, 1/88.
Laser Diodes Products Inc. Brochures for Model Nos. LVP1000 and LDP2QW (1988).
Efficient Laser Diode Side Pumped Neodymium Glass Slab Laser, Hanson et al, IEEE J of Quant. Elect., vol. 24, No. 9, p. 1811, 9/88.

Primary Examiner—Frank Gonzalez
Assistant Examiner—Susan S. Morse
Attorney, Agent, or Firm—Nixon & Vanderhye

[57] ABSTRACT

Various examples of an optically pumped laser are described. In each example, a laser member formed from active laser material is located in an optical cavity and a source of pumping light is arranged so that pumping light passes into the laser member through a side surface. A deflecting means is provided which ensures that the pumping light makes an initial pass followed by at least one, and preferably at least two, further passes across the laser member. In the further passes, the pumping light has a substantial component long the optical axis. Consequently, a relatively long absorption path for the pumping light is achieved. In one example, the laser member is an Nd:YAG bar (20), the pumping light source is an array (23) of laser diodes, and the deflecting means takes the form of a series of facets (27) formed along a side of the bar (20). In another example, the deflecting means is a diffraction grating.

7 Claims, 7 Drawing Sheets

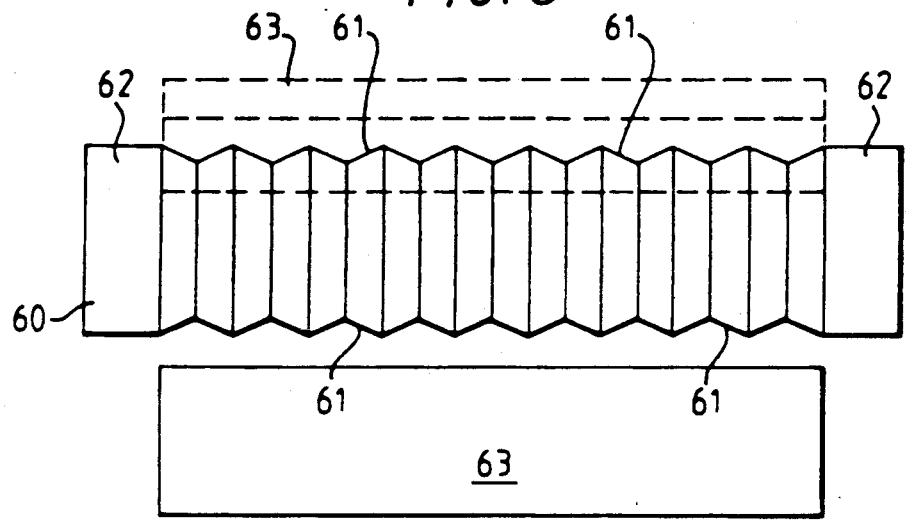
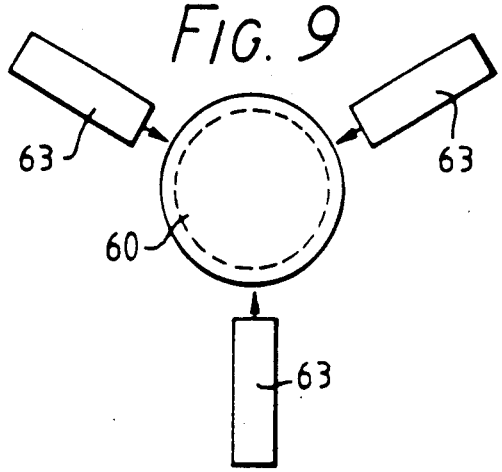
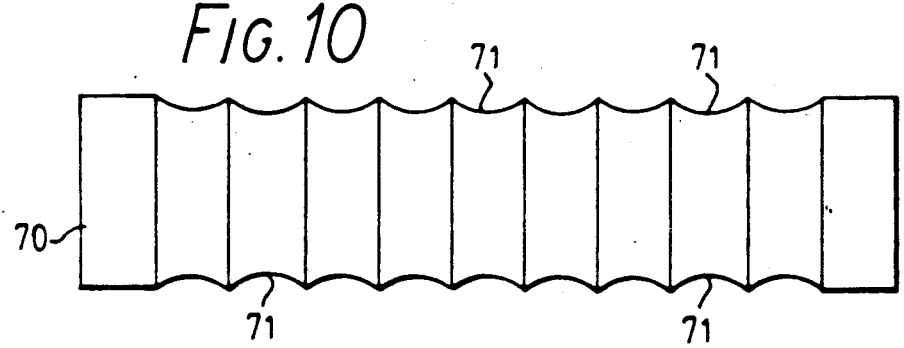

OPTICALLY PUMPED LASERS

FIELD OF THE INVENTION

This invention relates to optically pumped lasers and particularly, but not exclusively, to solid-state lasers pumped by laser diodes or light emitting diodes.

BACKGROUND AND SUMMARY OF THE INVENTION

It has been known for over a decade that light emitting diodes and laser diodes make attractive light sources for pumping solid-state lasers. Laser diodes are capable of achieving high electrical to optical conversion efficiencies. The most efficient and powerful laser diodes are currently fabricated from GaAlAs and such lasers typically operate in the 780 to 880 nm wavelength range. Laser diodes of this type have been produced with an electrical to optical conversion efficiency in excess of 50%. Unfortunately, the beam from a laser diode is far from ideal for most conventional laser applications. At high powers, laser diodes generally operate in a large number of optical modes resulting in an output beam having a large divergence (typically 10° by 40°) and the output beam is generally of very poor coherence. However, by using one or more laser diodes as a light source for pumping a solid state laser, the light from the laser diodes may be converted into highly coherent light. Moreover, the emission wavelengths from laser diodes can be made to coincide very well with strong absorption bands of several lasing ions, such as neodymium, and so high optical to optical conversion efficiency can be achieved between the pumping light and the laser light.

In solid-state lasers pumped by laser diodes, two geometries are known for supplying the pumping light to the laser medium. In the end-pumped geometry, the pumping light is delivered to the laser medium along the axis of the optical cavity and through an end face of the laser medium. With this end-pumped geometry it is relatively easy to match the laser mode volume (volume in which the lasing process occurs) with the pumped volume and to achieve a relatively long absorption path for the pumping light. Thus, a relatively high optical to optical conversion efficiency may be achieved. However, the power that may be achieved in the end-pumped geometry is restricted by the requirement to focus the pumping light to a small spot. For example, in U.S. Pat. No. 4,710,940, there is described a laser having the end-pumped geometry in which an overall efficiency of 8% is achieved but with a continuous wave output power of only 80 mW.

In the side-pumped geometry, the pumping light passes through a side face of the laser medium in a direction generally perpendicular to the axis of the optical cavity. With the side-pumped geometry, the laser medium can be pumped with a multiplicity of one or two dimensional arrays of laser diodes and so this geometry does not suffer from the power restriction of the end-pumped geometry. In a typical arrangement using the side-pumped geometry, the absorption path for the pumped light is relatively short and the pumped volume is much larger than the laser mode volume in the laser medium; consequently, the optical to optical conversion efficiency is low. In "Laser Diode Side Pumping of Neodymium Laser Rods", Frank Hanson et al, Applied Optics, Volume 27, January 1988, there is described a laser using a side-pumped geometry in which a reflective coating is placed around part of the circumference of a laser rod. The reflective coating provides a double pass of the pumping light and thereby improves absorption and hence efficiency. However, this increase in efficiency is achieved at the expense of beam quality.

It is an object of this invention to provide a new or improved optically pumped laser in which the above mentioned problems are overcome or reduced.

According to this invention there is provided an optically pumped laser comprising an optical cavity having an optical axis, a laser member located in the optical cavity and formed at least partly from active laser material, means for providing pumping light and arranged so that the pumping light passes into the laser member through at least one side surface thereof, and means for deflecting the pumping light so that pumping light initially travelling from the pumping light providing means towards the laser member in a direction normal to the optical axis is deflected and caused to make at least one pass across the laser member in a direction having a substantial component along the optical axis.

By deflecting the pump light so that it makes at least one pass across the laser member in a direction having a substantial component along the optical axis a relatively long absorption path for the pumping light may be achieved. Also, in the laser of this invention, the pumping volume may be closely matched to that required for the laser mode volume. Consequently, a relatively high overall electrical to optical efficiency may be achieved in a laser embodying this invention.

Preferably, the deflecting means is arranged so that light initially travelling in a direction normal to the optical axis is caused to make at least two passes across the laser member in directions having substantial components along the optical axis.

BRIEF DESCRIPTION OF THE DRAWINGS

This invention will now be described in more detail, by way of example, with reference to the drawings in which:

FIG. 8 is a sketch of part of a laser according to a third embodiment of this invention showing a laser rod and three arrays of laser diodes;

FIG. 9 is an end view of the laser of FIG. 8 showing the laser rod and the arrays of laser diodes;

FIG. 10 is a side view of a laser rod used in a laser according to a fourth embodiment of this invention;

DETAILED DESCRIPTION

Figure 1:
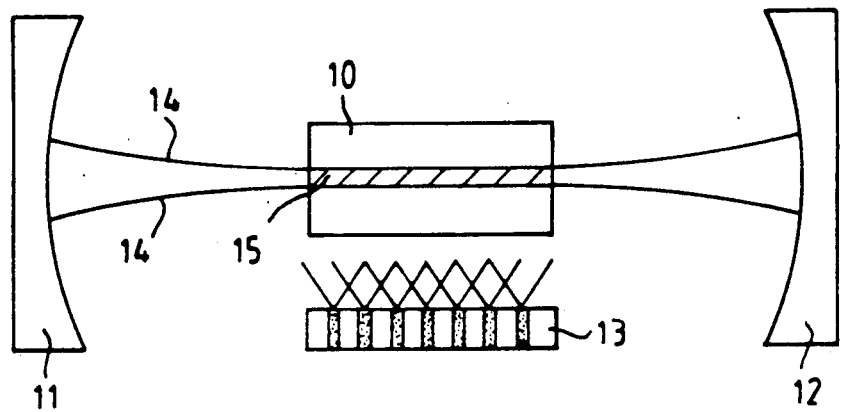
FIG. 1 is a diagram of a prior art laser using side-pumped geometry.

Referring now to FIG. 1, there is shown a prior art laser using a side-pumped geometry. This laser comprises a rod 10 of active laser material, for example an Nd:YAG crystal, located in an optical cavity formed by a pair of concave mirrors 11, 12. The mirror 11 is coated for high reflection at the lasing wavelength whereas the mirror 12 is coated for 95% reflection at this wavelength. The rod 10 is pumped by a linear array of laser diodes 13 which transmit pumping light through a side surface of rod 10 and thus in a direction generally perpendicular to the axis of the optical cavity. The volume of the optical cavity occupied by the laser light is indicated by the lines 14 and the part of this volume which is within the rod 10 is shown hatched and indicated by reference numeral 15. The volume delineated by lines 14 is known as the laser mode volume. The light from the laser diodes 13 occupies substantially the whole of the volume of the rod 10. Thus, the laser mode volume in rod 10 is much less than the pumping volume and there is a substantial mismatch between these two volumes. Also, in the laser shown in FIG. 1, the length of the absorption path of the pumping light in the rod 10 is relatively short. The mismatch of the pumping volume and the laser mode volume together with the short absorption length together result in a relatively low optical to optical conversion efficiency for the pumping light to the laser light.

Figure 2:
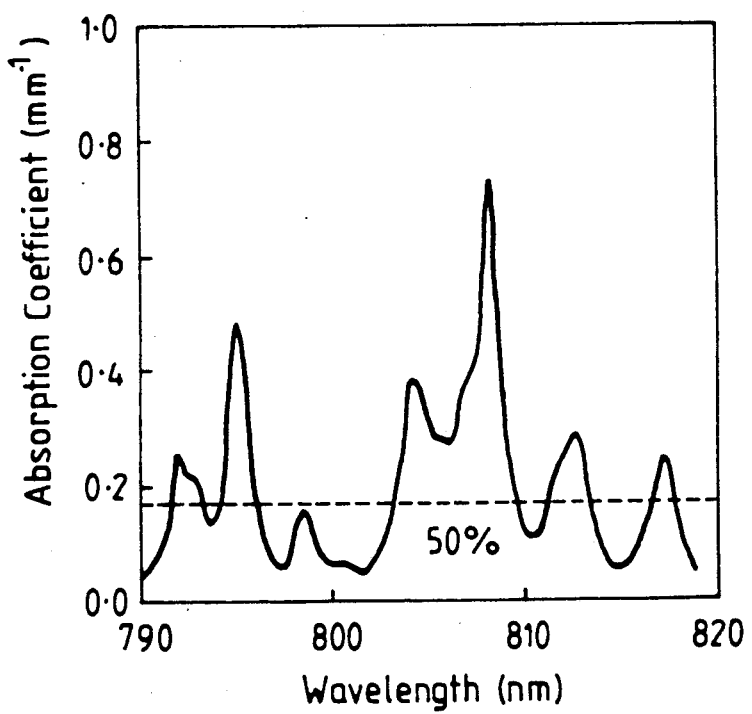
FIG. 2 is a graph of the absorption spectrum for Nd:YAG material.

Referring now to FIG. 2, there is shown an absorption spectrum for 1% doped Nd:YAG crystal. The dashed line indicates the value of the absorption coefficient at which 50% of the light is absorbed with a 4 m path length. A typical value for the length of the absorption path for the pumping light in the arrangement shown in FIG. 1 is less than 4 mm. As can be seen from FIG. 2, the widest and deepest absorption line occurs between 805 and 810 nm and has a width of approximately 5 nm. Typically, the spectral width of light emitted by a GaAlAs laser diode is of the order of 2 to 3 nm and this wavelength shifts by about 0.25 nm per °C. change in junction temperature. Consequently, when using such a laser diode to pump an Nd:YAG crystal the laser diode must be carefully matched to the absorption spectrum of the crystal and the temperature of the laser diode must be controlled within 5° C. to avoid serious detuning and loss in overall efficiency.

With the absorption spectrum shown in FIG. 2, it may be shown that a major relaxation on the matching requirement between the laser diode and the laser crystal and also on the temperature control of the laser diode may be achieved by increasing the absorption path to a value in excess of 10 mm. More particularly, with an absorption path length of 10 mm, the average absorption between 790 and 823 nm is in excess of 70%. As will now be explained, the present invention makes it possible to achieve an absorption path length in excess of 10 mm in a laser crystal having a width of only a few millimeters.

Figure 3:
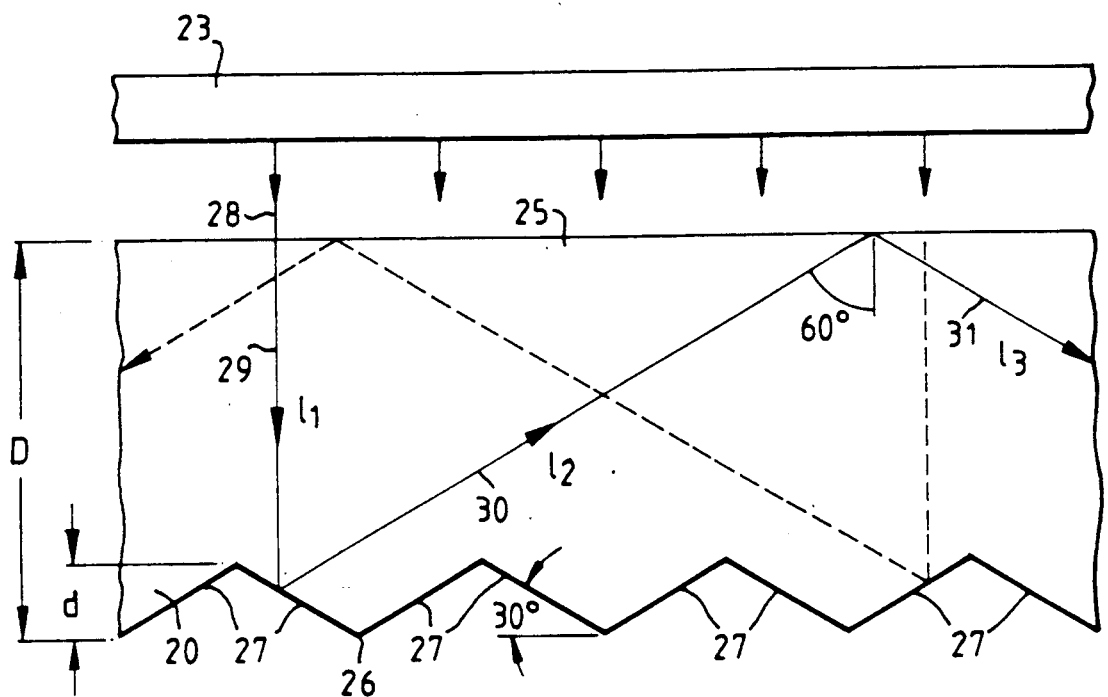
FIG. 3 is a sketch of part of a laser according to a first embodiment of this invention.
Figure 4:
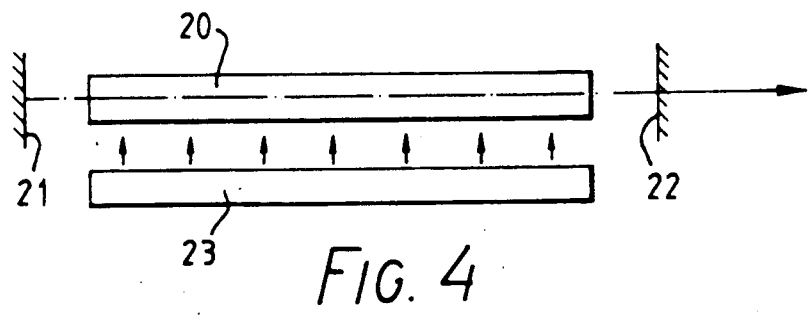
FIG. 4 is a diagram of the laser of FIG. 3.

Referring now to FIGS. 3 and 4, there is shown a laser according to a first embodiment of this invention. This laser comprises a laser member or bar 20 having a rectangular cross section and formed from an active laser material. In this example, the material is Nd:YAG crystal. The bar 20 is located between a pair of mirrors 21, 22 which together form an optical cavity, the bar 20 extending along the optical axis. The mirrors 21 and 22 are coated in a manner similar to that described with reference to FIG. 1. The bar 20 is pumped by a linear array 23 of laser diodes fabricated from GaAlAs. These laser diodes emit light at a wavelength of approximately 810 nm and such arrays are commercially available from a number of sources, for example, Spectra Diodes Laboratories Inc, San Jose, Calif., USA. The bar 20 may be cooled with either air or water.

As shown in FIG. 3, the side surface 25 of the bar 20 facing the laser diodes 23 is flat whereas the opposite side surface 26 is provided with a series of undulations or facets 27. Each of the facets 27 is inclined to the optical axis by an angle of 30°. The facets 27 are coated so that they are totally reflecting at the wavelength of the pumping light.

The path taken by the pumping light through the bar 20 will be described with reference to a beam 28 from one of the laser diodes. After entering the bar 20 through side surface 25, this beam makes an initial pass 29 across the bar 20 and is then incident on one of the facets 27. This initial pass has a length of $l_1$. At the facet 27, the beam 28 is reflected back into the bar 20 after being deflected through an angle of 60°. Consequently, the beam 28 makes a first reflected pass 30 having a length $l_2$ across bar 20. At the end of the first reflected pass 30, the beam 28 reaches the side surface 25 with an angle of incidence of 60°. The refractive index of the Nd:YAG crystal is 1.82 and the refractive index of water is 1.33. Thus, where the bar 20 is cooled by water, the critical angle for internal reflection is 47°. Where the bar is cooled with air, the critical angle is 33.3°. Thus, regardless of whether the bar 20 is cooled by air or water, the beam 28 will be totally internally reflected at the surface 25 with the result that it will make a second reflected pass 31 having a length $l_3$ across bar 20. During each reflected pass, the beam 28 travels in a direction having a major component along the optical axis.

The bar 20 has a width D and the facets 27 have a width of d. By making the period of the facets small, the effective aperture of bar 20 will tend to D. It may readily be shown that the length $(l_1+l_2+l_3)$ of the absorption path of the pumping light in bar 20 is approximately equal to 5D. Consequently, with a bar having a width of 2 mm, an absorption path length of approximately 10 mm may be achieved. Thus, the arrangement shown in FIGS. 3 and 4 permits high absorption of the pumping light without close matching of the spectrum of the laser diodes to the absorption peak of the active laser material and without tight temperature control. Also, in the arrangement shown in FIGS. 3 and 4, a major part of the volume of the bar 20 forms the laser mode volume and so there is close matching between this laser mode volume and the pumping volume.

Figure 5:
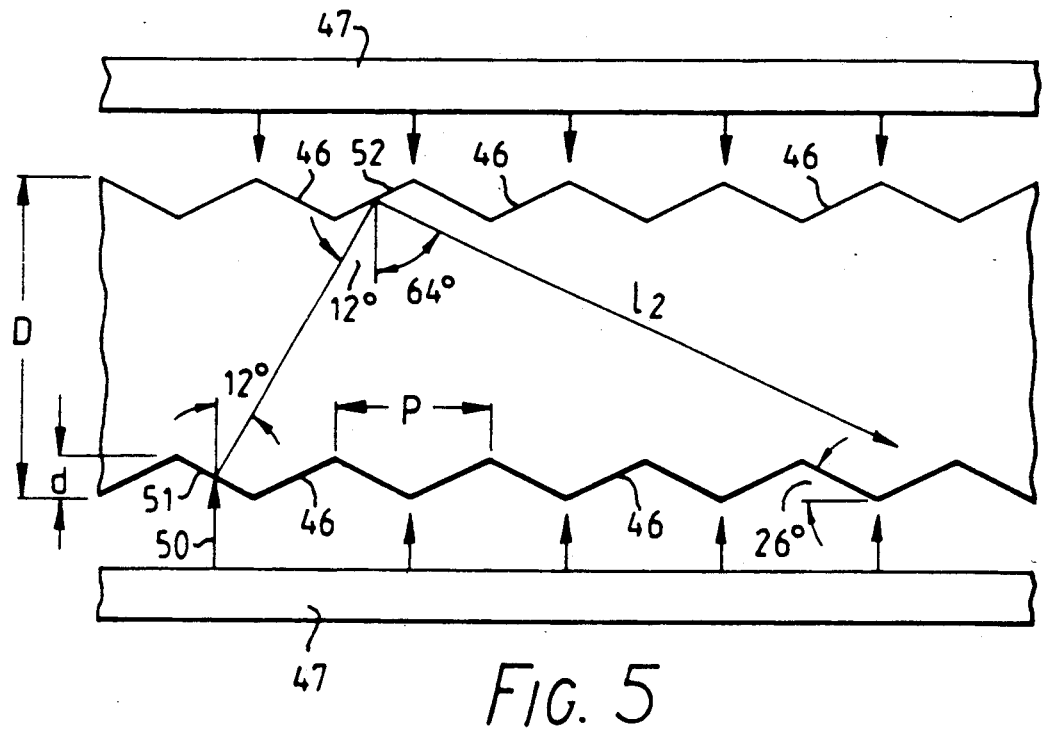
FIG. 5 is a sketch of part of a laser according to a second embodiment of this invention.
Figure 6:
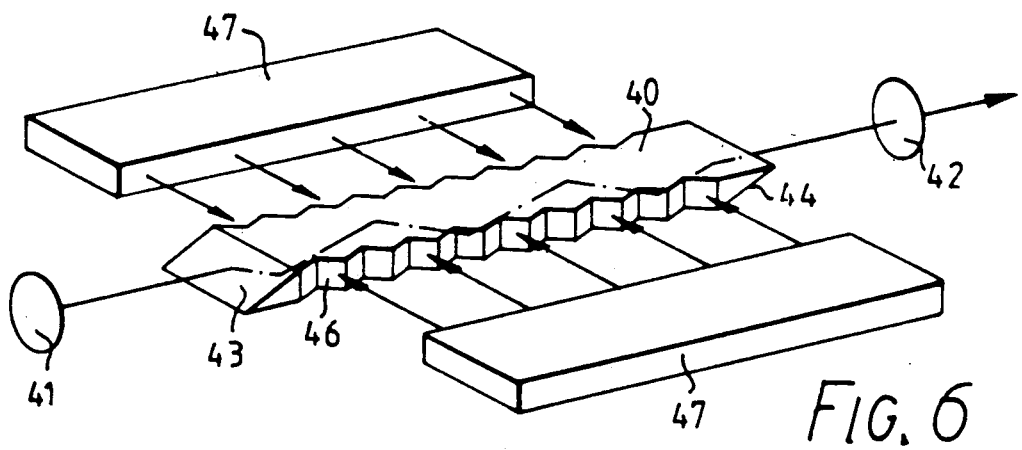
FIG. 6 is a diagrammatic perspective view of the laser of FIG. 5.
Figure 7:
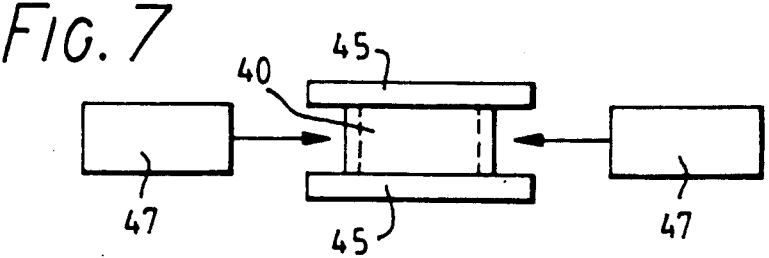
FIG. 7 is a diagrammatic cross-sectional view of the laser of FIG. 5.

Referring now to FIGS. 5 to 7, there is shown a slab laser according to a second embodiment of this invention. This slab laser comprises a laser member 40 formed from an Nd:YAG crystal located in an optical cavity formed by a fully reflecting mirror 41 and a mirror 42 which is partially reflecting at the wavelength of the laser light. The end faces 43, 44 are cut so that they are inclined to planes which are orthogonal to the axis of the optical cavity so that the laser beam makes multiple reflections upon the upper and lower surfaces of member 40. These upper and lower surfaces are optically polished and, as shown in FIG. 7, provided with sapphire cooling plates 45. A series of facets, some of which are indicated by reference numeral 46, is formed on each of the side surfaces of member 40. The member 40 is pumped by a pair of arrays 47 of laserr diodes, each of which is similar to the array 23 of FIG. 3 and each of which transmits pumping light through a respective side surface of member 40. The member 40 is cooled by air. The arrangement of the laser shown in FIGS. 5 to 7 provides a laser beam having an elliptical cross section which occupies most of the cross section of member 40. Thus, the laser mode volume is well matched to that of the pumping volume.

As will now be explainned with reference to FIG. 5, by a suitable combination of facet angle, the facet period p and the width D of member 40, a major part of the pumping light can have a path length of at least 4.3 times the width D of member 40 and the useful (unobstructed) aperture of member 40 can remain at over 90% of its cross section.

In the arrangement shown in FIG. 5, the facets 46 are inclined at an angle of 26° to the optical axis and the facets on one side surface are formed so as to be a mirror image of the facets on the other side surface with respect to the optical axis. As a beam 50 enters the member 40, it is refracted at a facet 51 through an angle of 12° and then makes an initial pass having a length $l_1$ across member 40. A major part of beam 50 will then be incident at an angle of 38° on a facet 52 on the opposite surface of member 40. Consequently, this major part of bem 50 will be totally internally reflected and thereby deflected through an angle of 76°. The outer parts of beam 50 will be incident on facets adjoining facet 52 and so these outer parts will not be totally internally reflected. After such reflection, the major part of beam 50 will make a first reflected pass having a length $l_2$ across member 40. Although not shown in FIG. 5, at the end of the first reflected pass, a major part of beam 50 will be incident at an angle of 38° on one of the facets 46 and will consequently be totally internally reflected to make a second reflected pass having a length $l_3$ across member 40. It may be shown that the total length of the initial pass and the first and reflected passes ($l_1+l_2+l_3$) is approximately 4.3D. At the end of the second reflected pass, part of beam 50 may be reflected again and so the absorption path length may be greater than 1.3D.

The facet period p and the width D of element 40 are chosen so that each beam travels approximately a whole facet period along the optical axis during the initial pass. Consequently, p is given by the following equation:

$$p = D \tan 12° = 0.214D \quad (1)$$

From the equation (1), it follows that the useful aperture of the element 40 is approximately 90% of its cross section.

Referring now to FIG. 8 and 9 there is shown part of a laser according to a third embodiment of this invention. This laser comprises a cylindrical laser rod 60 formed from an Nd:YAG crystal. A series of undulations, some of which are denoted by reference numeral 61, are formed on the outer surface of rod 60 between two end sections 62. Each of the undulations 61 extends around the circumference of rod 60 and has a V-shaped cross section. The rod 60 has a diameter of 2 mm and a length of 15 mm and is located in an optical cavity similar to that described with reference to FIG. 3 and 4. The rod 60 is pumped by three linear arrays 63 of laser diodes, each of the arrays being similar to the array 23 of FIGS. 3 and 4. The arrays 63 are equiangularly spaced around the circumference of rod 60. By a suitable combination of the diameter of rod 60, the period of undulations 61 and their angle of inclination to the optical axis, it may be arranged that each pumping beam will make at least three passes of rod 60. Thus, an absorption path length of approximately 10 mm may be achieved.

Referring now to FIG. 10 there is shown a rod 70 forming part of a laser according to a fourth embodiment of this invention. The rod 70 is generally similar to rod 60 except that it is provided with undulations 71 each of which has a U-shaped cross section. The rod 70 is pumped by three arrays of laser diodes in a manner similar to that described with reference to the laser FIG. 8 and 9.

Figure 11:
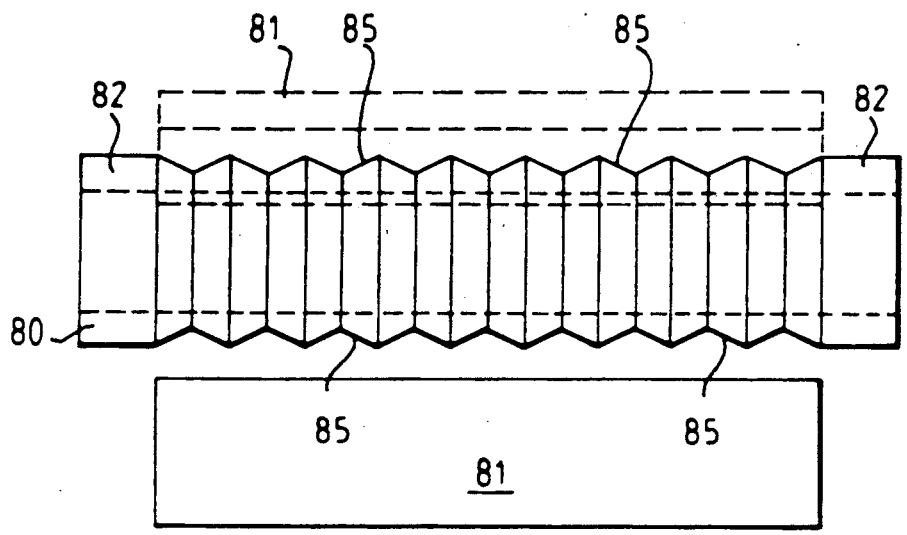
FIG. 11 is a sketch of part of a laser according to a fifth embodiment of this invention showing a laser rod and three arrays of laser diodes.
Figure 12:
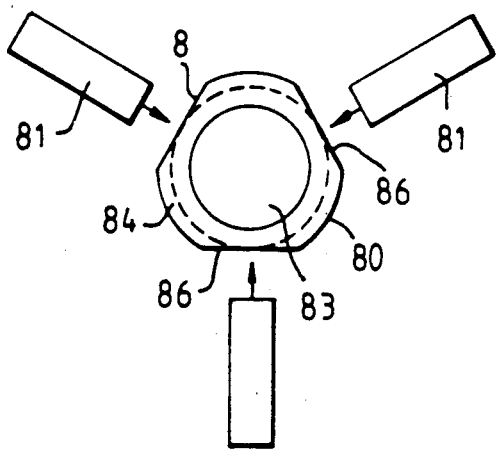
FIG. 12 is an end view of the laser of FIG. 11 showing the laser rod and the arrays of laser diodes.

Referring now to FIG. 11 and 12, there is shown part of a laser according to a fifth embodiment of this invention. This laser comprises a rod 80 which is pumped by three linear arrays of laser diodes arranged relative to rod 80 in a manner similar to that described with reference to FIGS. 8 and 9. Each of the arrays 81 is similar to the array 23 and the rod 80 together with the arrays 81 are located in an optical cavity similar to that described with reference to FIGS. 3 and 4.

The rod 80 comprises an inner cylindrical part 83 formed from an Nd:YAG crystal and an outer sleeve 84 formed from a material optically matched to the Nd:YAG crystal. The sleeve 84 is provided with undulations 85 similar to the undulations 61 of FIGS. 8 and 9. Three polished facets 86 are formed on the undulations 85, each of the facets 86 facing one of the linear arrays 81. The undulations 85 are arranged so that each pumping beam makes at least an initial pass followed by two reflected passes across rod 80. The rod 80 has a diameter of 2 mm and so an absorption path length of 10 mm may be achieved.

Figure 13:
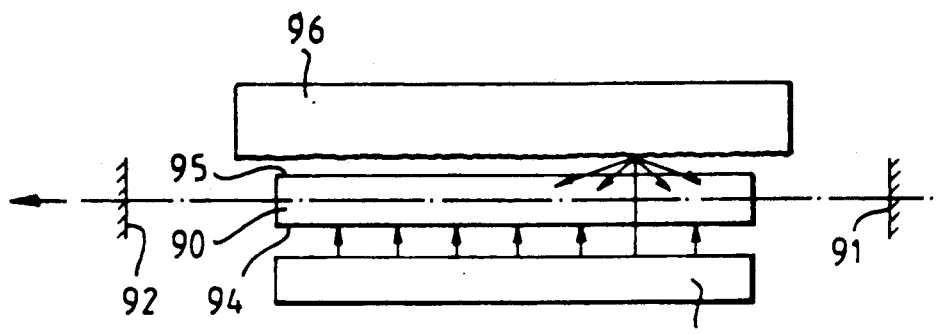
FIG. 13 is a diagram of a laser according to a sixth embodiment of this invention.
Figure 14:
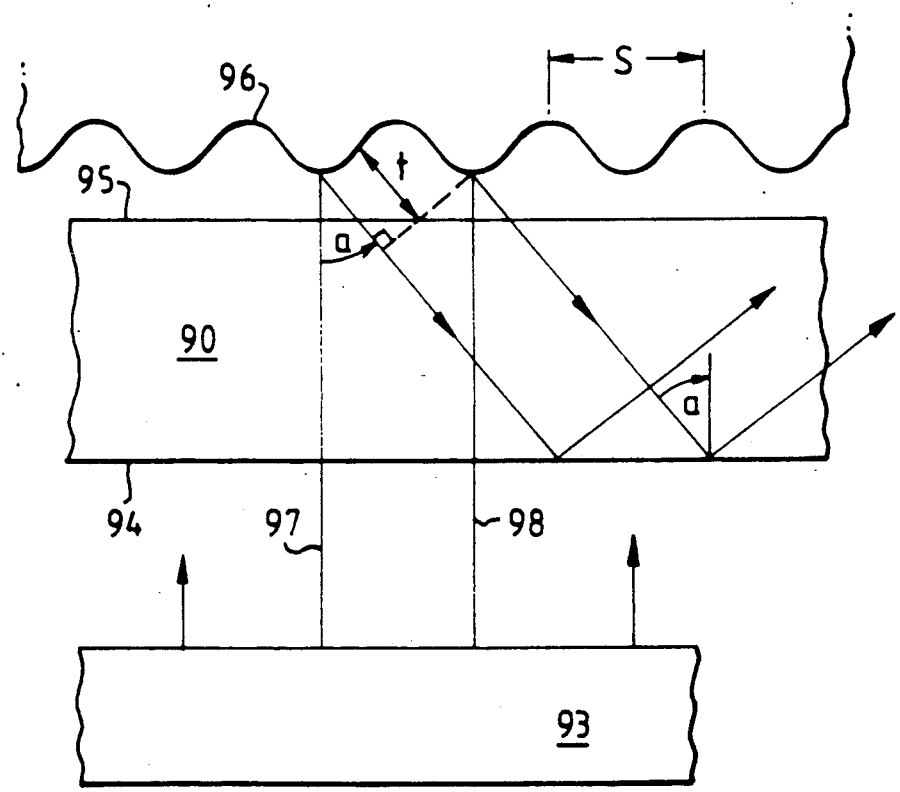
FIG. 14 is a diagram on an enlarged scale of part of the laser of FIG. 13 illustrating the geometry of the pumping arrangement.

Referring now to FIGS. 13 and 14, there is shown a laser according to a sixth embodiment of this invention. This laser comprises a laser member 90 having a rectangular cross section and formed from Nd:glass. The member 90 is located in an optical cavity formed by a totally reflecting mirror 91 and a mirror 92 which is partially reflecting at the wavelength of the laser light. A linear array 93 of laser diodes, similar to the array 23, transmits pumping light through a side surface 94 of member 90. Located adjacent the opposite side surface 95, there is provided a diffraction grating 96 of the reflection type. Alternatively, the diffraction grating can be formed directly on laser member 90. Although not shown, the space between the grating 96 and member 90 is filled with a liquid which has a refractive index closely matching that of member 90 and which can be circulated to cool member 90. As will be explained with reference to FIG. 14, the grating 96 reflects the pumping light so that it makes two reflected passes across member 90 after the initial pass.

Referring now to FIG. 14, the grating 96 has a regular profile having a period s. As shown, the profile is sinusoidal but other profiles, for example blazed, may be used. The passage of the pumping light through the member 90 will be described with reference to a pair of rays 97,98 which are reflected from similar points on adjacent periods of grating 96. After such reflection, the difference in path length between the rays 97,98 is t and constructive interference will occur when:

$$t = m\lambda/n \quad (2)$$

where m is an integer, λ is the wavelength of the pumping light in free space and n is the refractive index of Nd:glass.

If the rays 97,98 are reflected by grating 96 through an angle a with constructive interference, then:

$$t = s \sin a \quad (3)$$

and so $$a = \sin^{-1}(m\lambda/ns) \quad (4)$$

For total internal reflection at the crystal/air surface 94, the condition that must hold is:

$$a > \sin^{-1}(1/n) \quad (5)$$

From equations (4) and (5), it follows that the condition for total internal reflection is:

$$m\lambda/ns > 1/n \quad (6)$$

giving $$s < m\lambda. \quad (7)$$

For first order diffraction energy to be totally reflected, the period s of the grating must be less than the wavelength of the pumping light. If this condition is met, it follows from equation (7) that any higher orders (m > 1) of diffraction energy will also be totally internally reflected from surface 94.

From this description, it follows that the pumping light can be made to make an initial pass followed by two reflected passes across member 90 and so a long absorption path length can be achieved. Also, in the laser shown in FIGS. 13 and 14, the pumping volume is well matched to the laser mode volume.

In each of the lasers embodying the invention described above, the pumping light make an initial pass across the laser member in a direction normal to the optical axis. At the end of the initial pass, the pumping light is reflected so that it makes a reflected pass. As a result of the reflection at the end of the initial pass, it travels in a direction having a substantial component along the optical axis. By way of modification, the pumping light may be deflected by an optical device, such as a holographic element or a prism arrangement, positioned between the laser diodes and the laser member so that, during the initial pass, it travels in a direction having a substantial component along the optical axis. With this modification, no special arrangement is needed for reflecting the pumping light after the initial pass. Providing the pumping light is deflected through a sufficiently large angle, it will undergo total internal reflection at the end of the initial pass.

Figure 15:
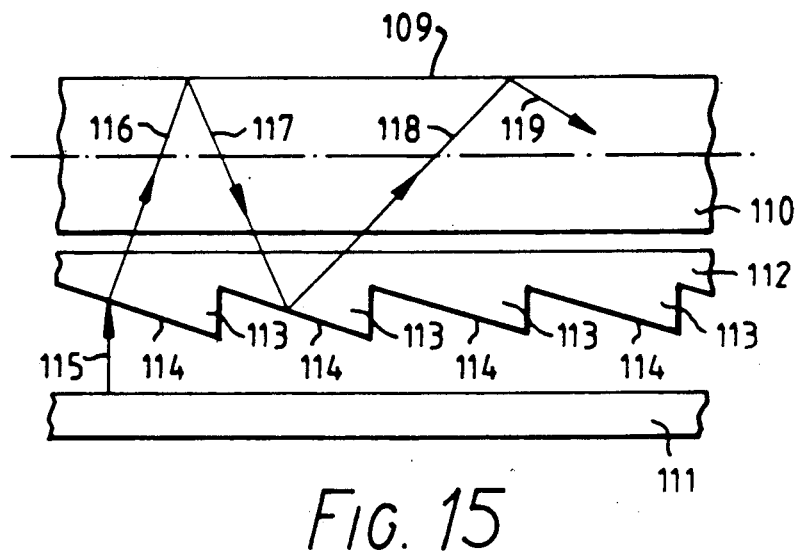
FIG. 15 is a diagram of a laser according to a seventh embodiment of this invention.

Referring now to FIG. 15, there is shown a laser which has an optical prism arrangement located between a laser member and an array of laser diodes. This laser comprises a laser bar 110 formed from an Nd:YAG crystal and located in an optical cavity similar to that described with reference to FIGS. 3 and 4. The bar 110 is pumped by a linear array 111 of laser diodes, similar to the array 23 of FIGS. 3 and 4. A prism arrangement 112 is located between array 111 and bar 110. On its side facing array 111, the prism arrangement 112 has a series of undulations 113 which collectively have a saw-tooth profile. The undulations 113 present a series of sloping faces 114 to array 111. A liquid having a refractive index approximately matching that of bar 110 and prism arrangement 112 flows between these two components. The side 109 of bar 110 remote from prism 112 has a highly reflective coating.

The path taken by the pumping light will be described with reference to a beam 115. As the beam 115 enters prism arrangement 112 at a face 114, it is refracted and thus deflected from its original direction. The beam 115 then makes an initial pass 116 across bar 110 in a direction having substantial component along the optical axis. At the end of the initial pass 116, the beam is reflected at side 109 and then makes a first reflected pass 117 across bar 110 and prism arrangement 111. At the end of reflected pass 117, the beam is totally internally reflected at a face 114 and so makes a second reflected pass 118. At the end of the second reflected pass 118, the beam is reflected at side 109 and makes a third reflected pass 119.

In each of the lasers embodying the invention described above, the active laser material is Nd:YAG or Nd:glass. Nd:glass has a wide absorption band in the vicinity of 810 nm and this aids in the efficient conversion of pumping light to laser light, particularly with an array of laser diodes not all having the same emission wavelengths. By way of modification other active materials may be used.

In the various examples described above, the pumping light is provided by laser diodes which emit light at a wavelength of approximately 810 nm. By way of modification, laser diodes may be used which emit light at wavelengths different from 810 nm, for example, at approximately 700 nm.

In the lasers which have been described above, in order to increase the output power the linear arrays may be replaced by two dimensional arrays of laser diodes. By way of another modification, light emitting diodes may be used in place of laser diodes.

Although the present invention has so far been described in relation to solid state lasers pumped by laser diodes or light emitting diodes, the present invention may also be used with other types of lasers which use a side-pumping geometry such as a laser pumped by flashlamps or a dye laser.

In relation to lasers pumped by flashlamps, the present invention is particularly suitable for a laser in which the laser member formed from active laser material has a small cross-sectional area as the absorption is normally short in such a laser. Each of the lasers embodying the invention described above may be modified to provide a laser pumped by flashlamps simply by replacing the laser diodes with one or more flashlamps.

Figure 16:
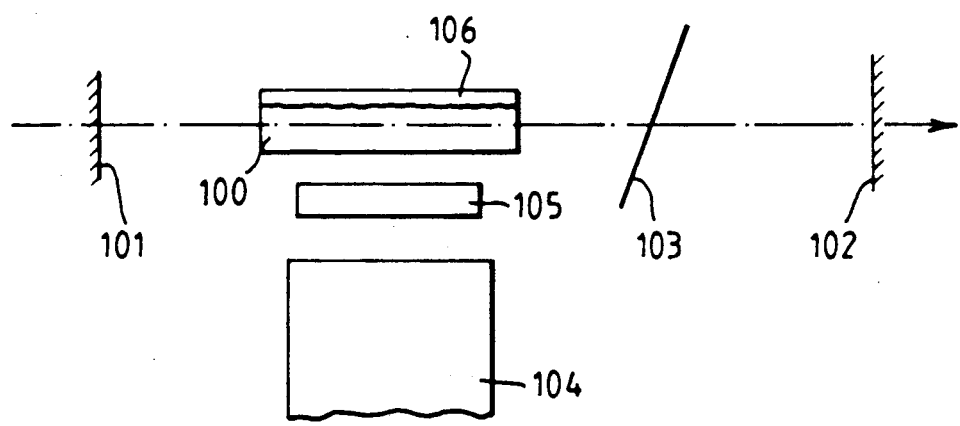
FIG. 16 is a diagram of a laser according to an eighth embodiment of this invention.

Referring now to FIG. 16 there is shown a dye laser embodying this invention. This laser comprises a cell 100 containing active laser material in the form of an organic dye dissolved in a solvent. The cell 100 is located in an optical cavity formed by a totally reflecting mirror 101 and a partially reflecting mirror 102, the optical cavity also containing a dielectric multilayer filter 103. The cell 100 is pumped by an Nd:YAG laser 104, the pumping light being focused by a cylindrical lens 105. The pumping light passes through one side surface of cell 100. A diffraction grating 106 is located inside the cell adjacent the other side surface. The diffraction grating 106 reflects pumping light after it is made an initial pass through cell 100.

In the laser shown in FIG. 16, the dye has a broad emission spectrum and the laser is tuned to a desired frequency by the filter 103. Thus, the dye laser of FIG. 15 represents an example of a tunable laser and the present invention may be used with other types of tunable lasers, one example of which is a Ti:sapphire laser. A Ti:sapphire laser embodying this invention would be generally similar to that shown in FIG. 3 except that the rod 20 would be formed from Ti:sapphire and the laser diode array 23 would be replaced by an Nd:YAG laser.

I claim:

1. An optically pumped laser comprising an optical cavity having an optical axis, a solid laser member located in the optical cavity and formed at least partly from active material, the laser member having two end surfaces which intersect the optical axis and at least one side surface extending between the end surfaces, pumping light providing means including at least one array of laser diodes for providing pumping light and arranged so that the pumping light passes into the laser member through at least one side surface thereof, and means for deflecting the pumping light so that pumping light initially travelling from the pumping light providing means towards the laser member in a direction normal to the optical axis is deflected and caused to make at least one pass across the laser member in a direction having a component along the optical axis.

2. A laser as claimed in claim 1, in which the deflecting means is arranged so that light initially travelling in a direction normal to the optical axis is caused to make at least two passes across the laser member in directions having components along the optical axis.

3. A laser as claimed in claim 1 or claim 2, in which the deflecting means comprises at least one optical device positioned between the pumping light providing means and the laser member.

4. A laser as claimed in claim 1, in which the deflecting means comprises means for reflecting pumping light back into the laser member after the pumping light has made an initial pass across the laser member so as to cause the pumping light to make a reflected pass across the laser member.

5. A laser as claimed in claim 4, in which the reflecting means is arranged to reflect the light in a direction which results in the light being totally internally reflected from the surface of the member after the light has made the first reflected pass, whereby the light makes a second reflected pass across the laser member.

6. A laser as claimed in claim 4 or claim 5, in which the reflecting means comprises at least one series of undulations formed on the surface of the laser member, the or each series of undulations extending along the laser member in a direction substantially parallel to the optical axis.

7. A laser as claimed in claim 4 or claim 5, in which the reflecting means comprises a diffraction grating of the reflection type.

* * * * *